United States Patent
Sukumaran et al.

(10) Patent No.: US 11,905,373 B2
(45) Date of Patent: Feb. 20, 2024

(54) TWO-DIMENSIONAL ORGANIC POLYMER AND DERIVATIVES THEREOF FOR SUPERCAPACITOR APPLICATIONS

(71) Applicant: Council of Scientific and Industrial Research, New Delhi (IN)

(72) Inventors: Santhosh Babu Sukumaran, Maharashtra (IN); Vivek Chandrakant Wakchaure, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 357 days.

(21) Appl. No.: 17/440,414

(22) PCT Filed: Mar. 18, 2020

(86) PCT No.: PCT/IN2020/050252
§ 371 (c)(1),
(2) Date: Sep. 17, 2021

(87) PCT Pub. No.: WO2020/188597
PCT Pub. Date: Sep. 24, 2020

(65) Prior Publication Data
US 2022/0162385 A1    May 26, 2022

(51) Int. Cl.
| | | |
|---|---|---|
| C08G 73/10 | (2006.01) | |
| C07D 209/48 | (2006.01) | |
| C07D 221/14 | (2006.01) | |
| C08L 27/22 | (2006.01) | |
| H01G 11/48 | (2013.01) | |

(52) U.S. Cl.
CPC ....... *C08G 73/1067* (2013.01); *C07D 209/48* (2013.01); *C07D 221/14* (2013.01); *C08G 73/1017* (2013.01); *C08L 27/22* (2013.01); *H01G 11/48* (2013.01)

(58) Field of Classification Search
CPC .................................................. C08G 73/1067
See application file for complete search history.

(56) References Cited

U.S. PATENT DOCUMENTS

2017/0240706 A1 * 8/2017 Wetzel .................. C08G 73/22

OTHER PUBLICATIONS

International Search Report dated Jun. 15, 2020 in reference to co-pending Indian Patent application No. PCT/IN2020/050252 filed on Mar. 18, 2020.
Written Opinion dated Jun. 15, 2020 in reference to co-pending Indian Patent application No. PCT/IN2020/050252 filed on Mar. 18, 2020.
Chandra, et al., "Interplaying Intrinsic and Extrinsic Proton Conductivities in Covalent Organic Frameworks", Chemistry of Materials, vol. 28, pp. 1489-1494, 2016.
Meng, et al., "Proton Conduction in 2D Aza-Fused Covalent Organic Frameworks", Chemistry of Materials, vol. 31, pp. 819-825, 2019.

(Continued)

*Primary Examiner* — William D Young
(74) *Attorney, Agent, or Firm* — Dinsmore & Shohl LLP

(57) ABSTRACT

The present invention provides two-dimensional polymers P1 and P2 of pyromellitic diimide and hexaamino benzene and derivatives thereof, from monomer of Formula (M), which are used to synthesize composites for supercapacitor applications. M

10 Claims, 6 Drawing Sheets

(56) References Cited

OTHER PUBLICATIONS

Sheberla, et al., "Conductive MOF electrodes for stable supercapacitors with high areal capacitance", Nature Materials, vol. 16, pp. 220-225, Feb. 2017.

Liao, et al., "Efficient Supercapacitor Energy Storage Using Conjugated Microporous Polymer Networks Synthesized from Buchwald-Hartwig Couplng", Advanced Materials, vol. 30, pp. 1705710 (1 of 10-10 of 10), 2018.

* cited by examiner

TWO-DIMENSIONAL ORGANIC POLYMER AND DERIVATIVES THEREOF FOR SUPERCAPACITOR APPLICATIONS

CROSS REFERENCES TO RELATED APPLICATIONS

This application is a national-stage application under 35 U.S.C. § 371 of International Application No. PCT/IN2020/050252, filed Mar. 18, 2020, which International Applications claims benefit of priority to Indian Patent Application No. 201911010587, filed Mar. 19, 2019.

FIELD OF THE INVENTION

The present invention provides two-dimensional polymer and derivatives thereof for enhanced supercapacitor applications. More particularly, the present invention provides two-dimensional polymers of pyromellitic diimide and hexaamino benzene and derivatives thereof, which are used to synthesize composites for supercapacitor applications.

BACKGROUND AND PRIOR ART OF THE INVENTION

Energy storage involves converting the form of energy which is not storable into a storable form. Energy storage means capturing the energy produced at one time for use at a later time. In this context, batteries and capacitors are good options for energy storage. Batteries can hold large amounts of power, but they take more time to charge up. On the other hand, capacitors are charging instantly but store only tiny amounts of power. Electrochemical Capacitors (ECs) also called supercapacitors are considered as best complementary to batteries for energy storage. ECs having high power density, extremely long durability and more reliable safety features.

A capacitor or a condenser is a two-terminal electrical device used to store energy electrostatically. A capacitor can be used like a temporary battery because it can store electric energy when disconnected from its charging circuit, or as other types of the rechargeable energy storage system. Capacitors are commonly used in electronic devices to maintain power supply while batteries change.

As if we consider our future energy requirements, when we need to store and release large amounts of electricity very quickly, it's quite likely to turn towards supercapacitors that combine the best of both batteries and capacitors. ECs have been widely applied in portable electronics (smartphones, laptops), power back-up devices, electric vehicles, etc. Functionalized carbons (FCs) have been extensively used for energy storage application but those do not meet the required standards.

Different polymers are synthesized using metal-based catalysts exhibiting electrical conductance. Some reports indicate that the trace metals contaminating the polymers are responsible for enhancing the conductance of such polymers and that the pristine polymer displays poor conductance.

The article titled "Conductive MOF electrodes for stable supercapacitors with high areal capacitance" by Dinca et al. published in the journal "*Nat. Mater.* 2017, 16, 220" reports $Ni_3(2,3,6,7,10,11$-hexaiminotriphenylene$)_2$ ($Ni_3(HITP)_2$), a MOF with high electrical conductivity.

The article titled "Efficient Supercapacitor Energy Storage Using Conjugated Microporous Polymer Networks Synthesized from Buchwald-Hartwig Coupling" by Yaozu Liao,* Haige Wang, Meifang Zhu, and Arne Thomas published in the journal "*Adv. Mater.* 2018, 30, 1705710" reports novel conjugated microporous polymer (CMP) networks are presented for supercapacitor energy storage, namely 3D polyaminoanthraquinone (PAQ) networks synthesized via Buchwald-Hartwig coupling between 2,6-diaminoanthraquinone and aryl bromides.

Still, there is a need in the art for the promising organic materials which can be easily synthesized, scaled up, from cheaply available resources.

OBJECTS OF THE INVENTION

The main objective of the present invention is to provide new two dimensional organic polymers and derivatives thereof exhibiting electrical conductance and process for the preparation thereof.

One more objective of the present invention is to provide supercapacitors comprising of composites of new two-dimensional polymer and process for the preparation thereof.

Acronyms Used in the Invention

| | |
|---|---|
| HAB | Hexaamino-benzene |
| DMSO | Dimethyl sulfoxide |

SUMMARY OF THE INVENTION

Accordingly, the present invention provides a two-dimensional organic monomer of formula M, corresponding polymers synthesized from monomer M and processes for the preparation thereof.

The embodiment of the present invention thus provides a two-dimensional organic monomer of formula M;

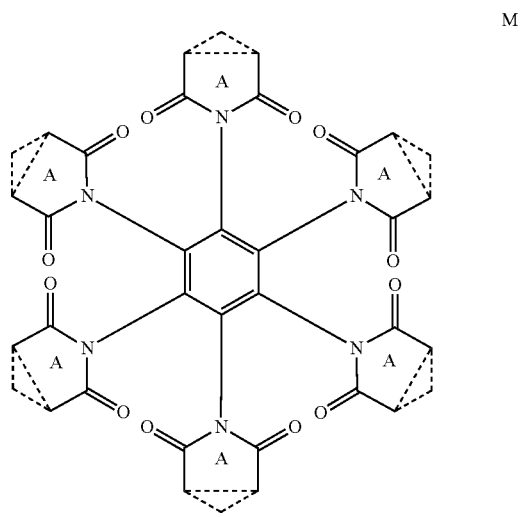

wherein, when ring A is 5 membered ring then it is fused with benzene ring at dotted bond; and when ring A is 6 membered ring then it is fused with two fused benzene rings at dotted bonds.

In a particularly preferred embodiment a two-dimensional organic monomer of formula M is formula M1 and formula M2;

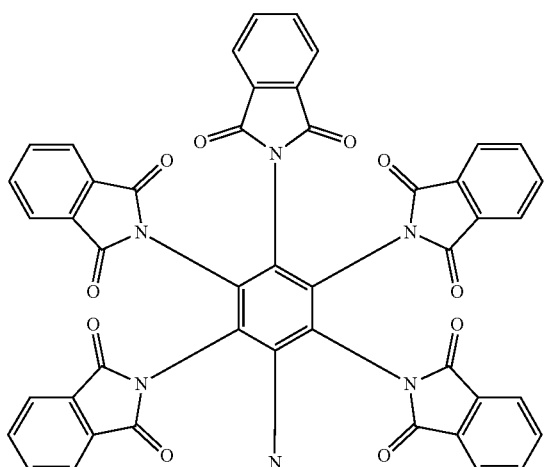

M1

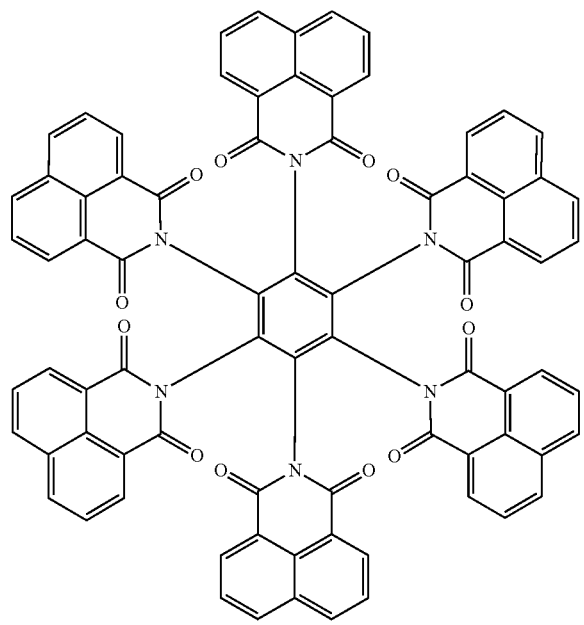

M2

Another embodiment of the present invention also provides a process for the preparation of monomer of formula M; wherein the process comprises the steps of:

i) charging HAB and compound of Formula (1) in a suitable solvent;

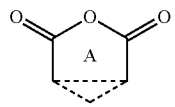

wherein, when ring A is 5 membered ring then it is fused with benzene ring at dotted bond; and when ring A is 6 membered ring then it is fused with two fused benzene rings at dotted bonds.

ii) refluxing the reaction mixture under argon atmosphere for a suitable period;

iii) distilling the reaction mixture at a suitable temperature and pressure;

iv) centrifuging the obtained solid from step iii) and washing with water and solvent;

v) performing the soxhlet extraction on obtained solid from step iv) with water, methanol, acetone for a suitable period; and vi) drying under vacuum to get dark green colored solid of formula M.

Compound of formula (1) is selected from phthalic anhydride and 1H, 3H-benzo[de]isochromene-1,3-dione (NMA).

The process is depicted below in scheme-1:

Scheme-1

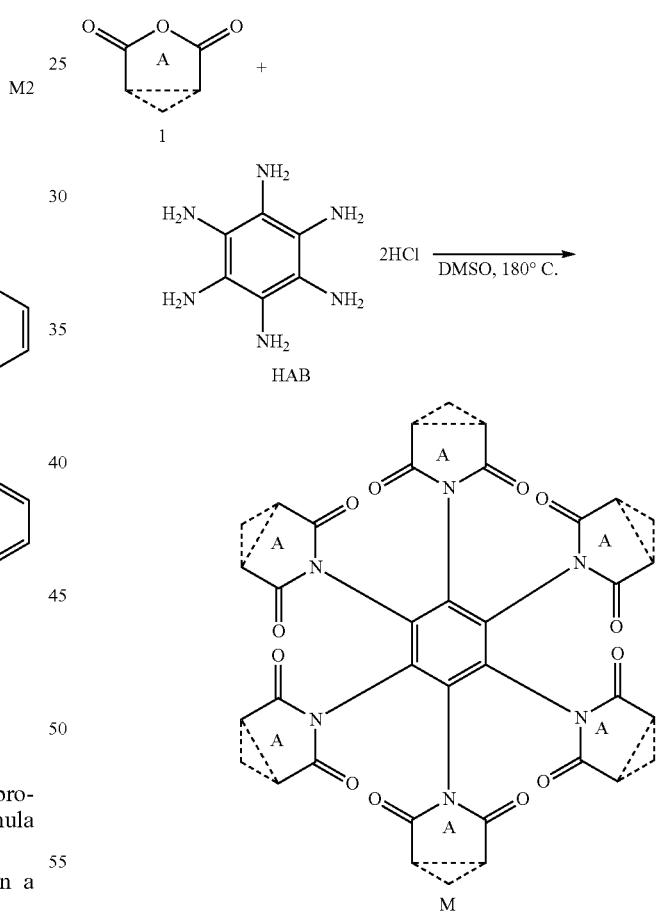

wherein, when ring A is 5 membered ring then it is fused with benzene ring at dotted bond; and when ring A is 6 membered ring then it is fused with two fused benzene rings at dotted bonds.

Yet another embodiment of the present invention provides a corresponding polymer synthesized from a monomer of formula M; wherein said polymers are selected from the polymers of formula P1 and formula P2.

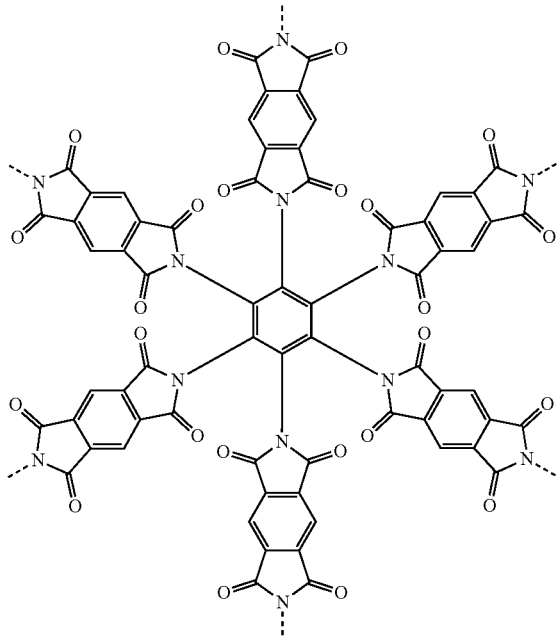

P1

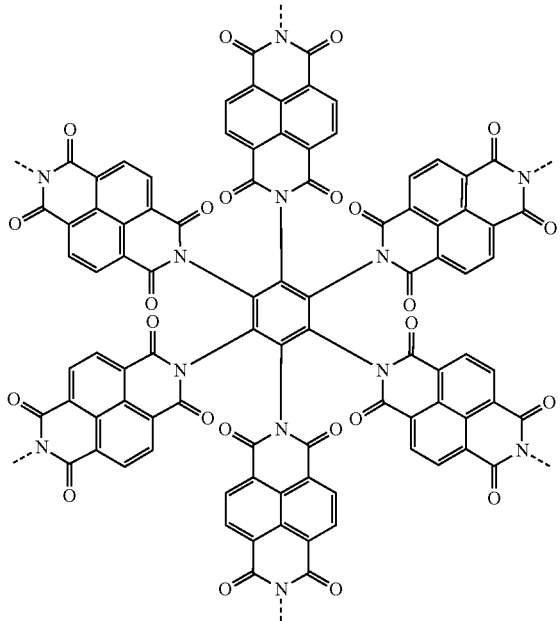

P2

Yet another embodiment of the present invention provides a general process for the preparation of polymer from monomer M; wherein said process comprises the steps of:
a) charging HAB and dianhydride compound (2) in a suitable solvent;
b) refluxing the reaction mixture under argon atmosphere for a suitable period;
c) distilling the reaction mixture at a suitable temperature and pressure;
d) centrifuging the obtained solid from step iii) and washing with water and solvent;
e) performing the soxhlet extraction on obtained solid from step iv) with water, methanol, acetone for a suitable period; and
f) drying under vacuum to get black colored solid of the polymer compound.

Dianhydride compound (2) is selected from pyromellitic dianhydride and Isochromeno[6,5,4-def]isochromene-1,3,6,8-tetrone (NDA).

Yet another embodiment of the present invention provides a composition for the supercapacitor applications. The polymer of formula P1 is porous and is doped with Carbon for the application in capacitors to increase conductivity. Different % composition of 10-40% polymer with 05% binder and the rest being carbon has been checked for capacitance. Composition with 30% polymer+05% binder+65% carbon found to provide good supercapacitor efficiency. 1M sulphuric acid is used as the electrolyte.

The process for the preparation of composite used in the supercapacitor application comprises of making the slurry of polymer, Activated Carbon (AC, YP-50F) and Nafion (binder) in Isopropyl Alcohol (IPA). The weight ratio of polymer:AC:binder on the cathode is 3:6.5:0.5. The mass loading is per electrode area of ~140 μg cm$^2$.

DETAILED DESCRIPTION OF THE INVENTION

Figure 1:
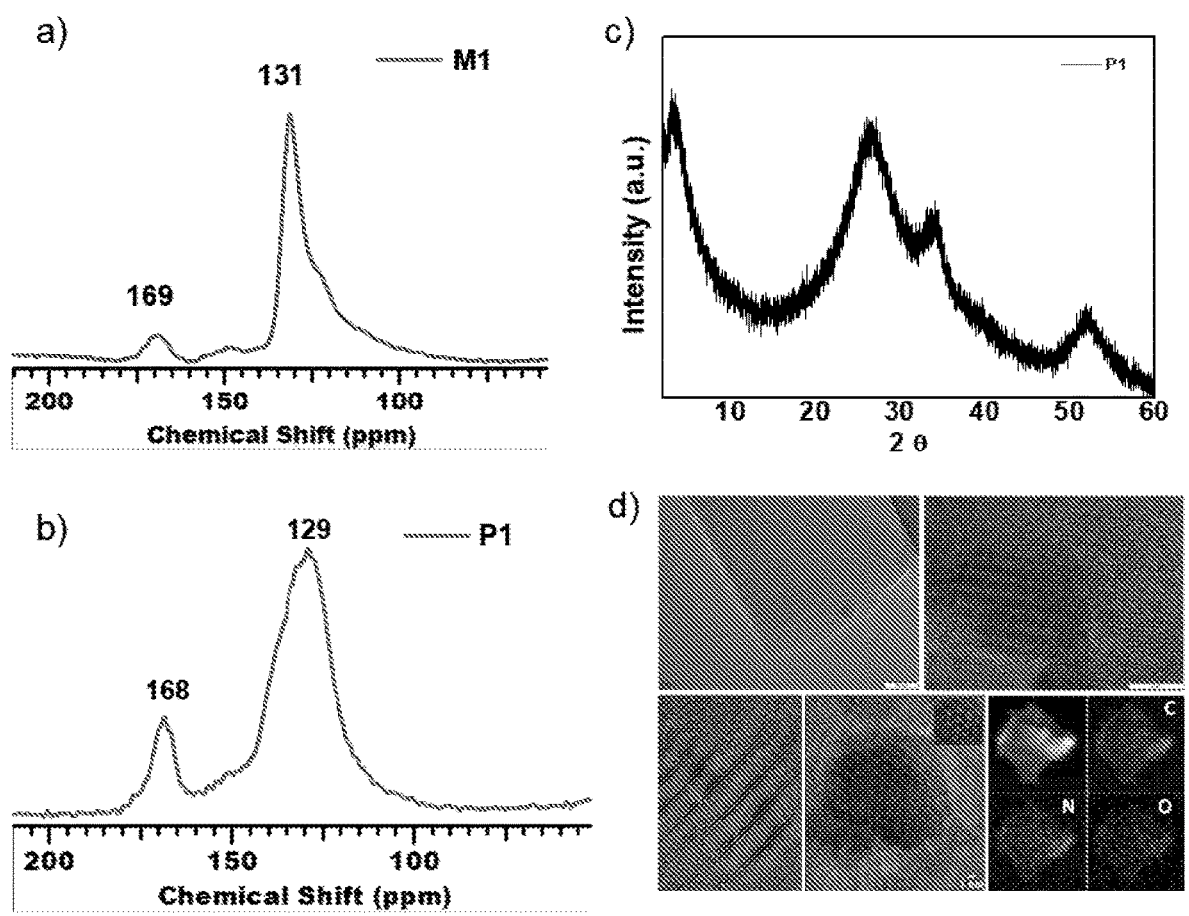
FIG. 1 shows (a) solid-state $^{13}$C NMR of a monomer of formula M1 (b) and polymer of formula P1; (c) PXRD of a polymer of formula P1 (d) and HR-TEM images with the corresponding elemental mapping of a polymer of formula P1.

The invention will now be described in detail in connection with certain preferred and optional embodiments, so that various aspects thereof may be more fully understood and appreciated.

Accordingly, the present invention provides a two-dimensional organic monomer of formula M, corresponding polymers synthesized from monomer M and processes for the preparation thereof.

The embodiment of the present invention thus provides a two-dimensional organic monomer of formula M;

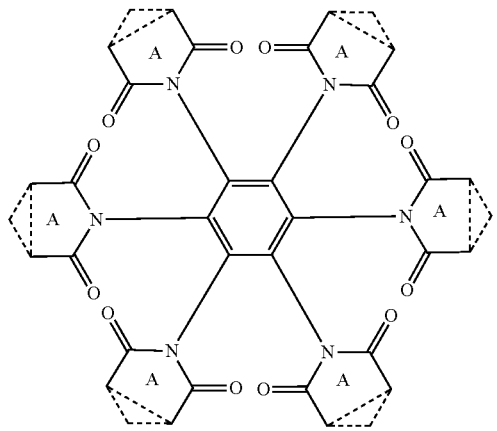

M wherein, when ring A is 5 membered ring then it is fused with benzene ring at dotted bond; and when ring A is 6 membered ring then it is fused with two fused benzene rings at dotted bonds.

In a particularly preferred embodiment a two-dimensional organic monomer of formula M is selected from a monomer of formula M1 and monomer of formula M2;

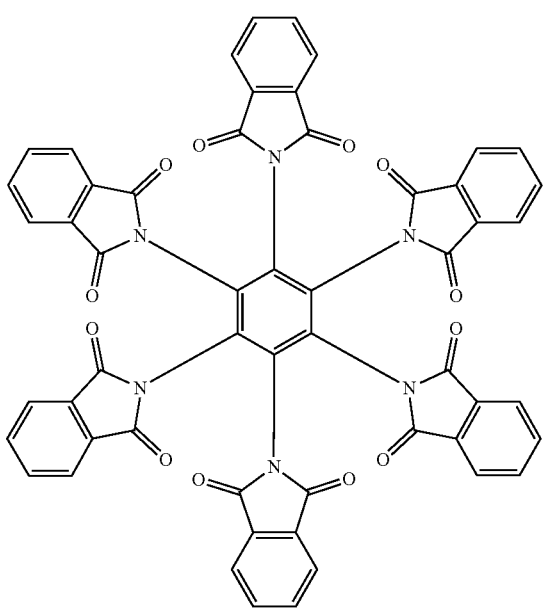

M1

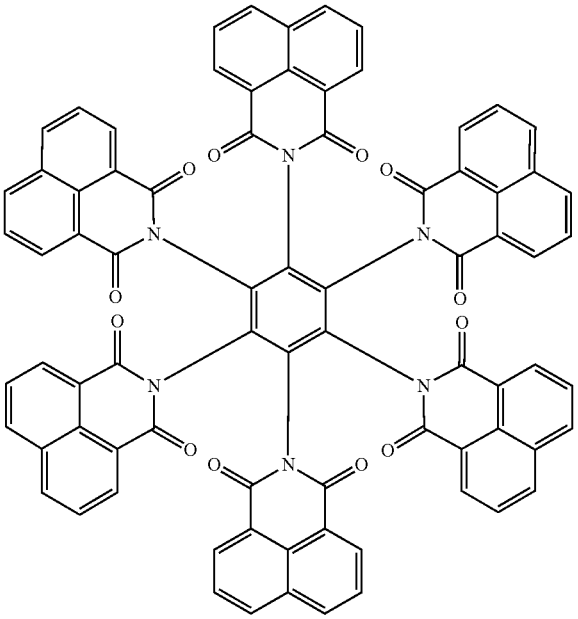

M2

Another embodiment of the present invention also provides a process for the preparation of monomer of formula M; wherein the process comprises the steps of:

i) charging HAB and anhydride compound of Formula (1) in a suitable solvent;

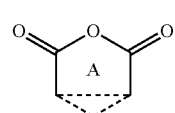

1 wherein, when ring A is 5 membered ring then it is fused with benzene ring at dotted bond; and when ring A is 6 membered ring then it is fused with two fused benzene rings at dotted bonds.

ii) refluxing the reaction mixture under argon atmosphere for a suitable period;

iii) distilling the reaction mixture at a suitable temperature and pressure;

iv) centrifuging the obtained solid from step iii) and washing with water and solvent;

v) performing the soxhlet extraction on obtained solid from step iv) with water, methanol, acetone for a suitable period; and vi) drying under vacuum to get dark green colored solid of formula M.

Anhydride compound of formula (1) is selected from phthalic anhydride and 1H, 3H-benzo[de]isochromene-1,3-dione (NMA).

The process is depicted below in scheme-1:

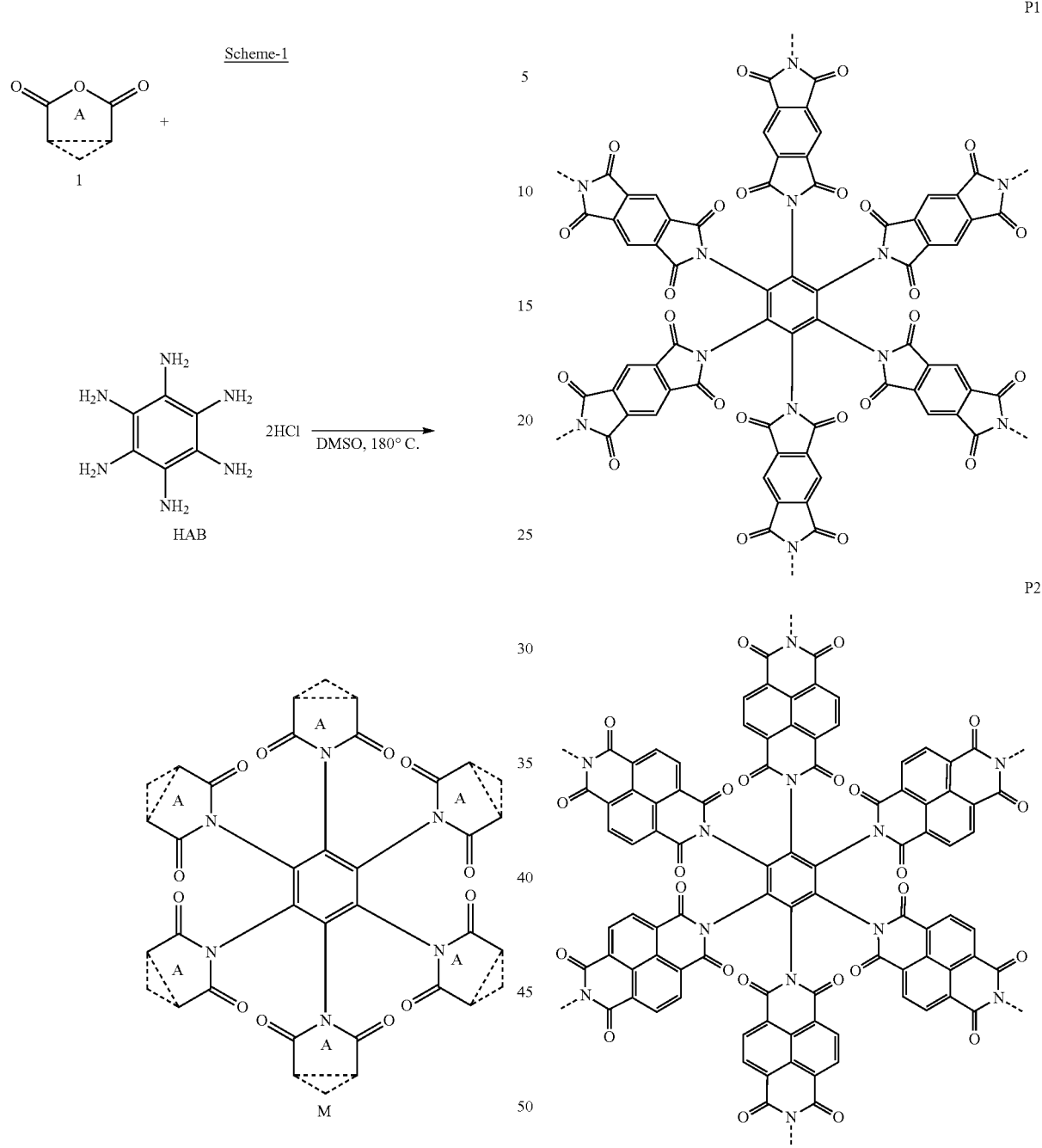

wherein, when ring A is 5 membered ring then it is fused with benzene ring at dotted bond; and when ring A is 6 membered ring then it is fused with two fused benzene rings at dotted bonds.

Yet another embodiment of the present invention provides a corresponding polymer synthesized from the monomer of formula M; wherein said polymers are selected from the polymers of formula P1 and formula P2.

Yet another embodiment of the present invention provides a general process for the preparation of polymer from monomer M; wherein said process comprises the steps of:
  a) charging HAB and dianhydride compound (2) in a suitable solvent;
  b) refluxing the reaction mixture under argon atmosphere for a suitable period;
  c) distilling the reaction mixture at a suitable temperature and pressure;
  d) centrifuging the obtained solid from step iii) and washing with water and solvent;
  e) performing the soxhlet extraction on obtained solid from step iv) with water, methanol, acetone for a suitable period; and f) drying under vacuum to get black colored solid of the polymer compound.

Dianhydride compound (2) is selected from pyromellitic dianhydride and Isochromeno[6,5,4-def]isochromene-1,3,6,8-tetrone (NDA).

The suitable solvent used in the above processes at step i) and a) may include the polar solvents, non-polar solvents, alcohol solvents, ether solvents, ester solvents, amide solvents and the mixtures thereof. Polar solvents may include water, ammonia, sulfuric acid, deuterium oxide, ethanol, methanol, acetone, isopropanol, methyl ethyl ketone, n-propanol, acetonitrile, DMSO, and DMF and mixtures thereof. Non-polar solvents may include chloroform, pentane, hexane, benzene, toluene, octane, decane, dimethyl ether, and dichloromethane, and mixtures thereof. Alcohol solvents may include methanol, ethanol, isopropanol, and mixtures thereof. Ether solvents may include tetrahydrofuran, diethyl ether, 1,4-dioxane, methyl tert-butyl ether, and mixtures thereof. Ester solvents include methyl acetate, ethyl acetate, isopropyl acetate, tert-butyl acetate, and mixtures thereof. In particularly useful embodiments, polar solvents are used and most preferably DMSO is used as a solvent at step i) and a).

A suitable period to maintain the reaction mixture at reflux temperature at step ii) and b) is 20-30 hr, more particularly 24 hr.

Suitable temperature and pressure at step iii) and step c), is 170-190° C. and 0-5 atm, respectively. More particularly temperature and pressure are 180° C. and 1 atm, respectively.

The suitable solvent used for washing at step iv) and d) along with water may include the polar solvents, non-polar solvents, alcohol solvents, ether solvents, ester solvents, and the mixtures thereof. Polar solvents may include water, ammonia, sulfuric acid, deuterium oxide, ethanol, methanol, acetone, isopropanol, methyl ethyl ketone, n-propanol, acetonitrile, DMSO, and DMF and mixtures thereof. Non-polar solvents may include chloroform, pentane, hexane, benzene, toluene, octane, decane, dimethyl ether, and dichloromethane, and mixtures thereof. Alcohol solvents may include methanol, ethanol, isopropanol, and mixtures thereof. Ether solvents may include tetrahydrofuran, diethyl ether, 1,4-dioxane, methyl tert-butyl ether, and mixtures thereof. Ester solvents may include methyl acetate, ethyl acetate, isopropyl acetate, tert-butyl acetate, and mixtures thereof. In particularly useful embodiments, polar solvents are used and most preferably acetone is used as a solvent at step iv) and d).

A suitable period for soxhlet extraction at step v) and e) is 35-40 hr, more particularly 36 hr.

Yet another embodiment of the present invention provides a composition for the supercapacitor applications. The polymer of formula P1 is porous and is doped with Carbon for the application in capacitors to increase conductivity. Different % composition of 10-40% polymer with 05% binder and the rest being carbon has been checked for capacitance. Composition with 30% polymer+05% binder+65% carbon found to provide good supercapacitor efficiency. 1M sulphuric acid is used as an electrolyte.

The process for the preparation of composite used in the supercapacitor application comprises of making the slurry of polymer, Activated Carbon (AC, YP-50F) and Nafion (binder) in Isopropyl Alcohol (IPA). The weight ratio of polymer:AC:binder on the cathode is 3:6.5:0.5. The mass loading is per electrode area of ~140 μg $cm^2$.

The capacitance of the several state-of-art promising electrode materials made up of different materials has been checked. The data is summarised below in Table-1:

TABLE 1

Comparison of areal ($mFcm^{-2}$) and gravimetric ($Fg^{-1}$) capacitances with state-of-art promising electrode materials made up of different materials. Sr. No. 31 and 32 show data for the new monomer of formula M1 and polymer of formula P1

| Sr. No | Material | Specific Capacitance ($mFcm^{-2}$) | Gravimetric capacitance ($Fg^{-1}$) | Electrolyte used | Surface Area ($m^2g^{-1}$) | Scan Rate/ Current Density | Cycle | Ratio |
|---|---|---|---|---|---|---|---|---|
| 1 | GNS/PANI composites | — | 1046 | 6M KOH | | 1 $mVs^{-1}$ | — | GNS/PANI:CB:PTFE (75:20:5) |
| 2 | GNS/CB | — | 175 | 6M KOH | 586 | 10 $mVs^{-1}$ | 6000 | GNS/CB (90:10) |
| 3 | PAG80 | — | 480 | 2M $H_2SO_4$ | 14.2 | 0.1 A/g | — | GO/PANI (80:20) |
| 4 | GPCP | | 233 | 1M $H_2SO_4$ | 39 | 20 $mVS^{-1}$ | 1500 | — |
| 5 | PANI/GO | | 531 | 1M $H_2SO_4$ | — | 200 mA/g | — | PANI/graphite oxide (100:1) |
| 6 | G-$PNF_{30}$ | | 210 | 1M $H_2SO_4$ | 12.7 | 0.3 A/g | 800 | — |
| 7 | DAAQ-TFP/carbon black | 0.4 | 48 +/− 10 | 1M $H_2SO_4$ | 435 | 10 $mVs^{-1}$ | 5000 | DAAQ-TFP:CB:PVDF (35:60:5) |
| 8 | DAAQ-TFP COF thin film | 3.0 | — | 1M $H_2SO_4$ | >1000 | 0.4 $mAcm^{-2}$ | 5000 | DAAQ-TFP:CB:PVDF (35:60:5) |
| 9 | DAAQ-TFP/PEDOT | 34 | — | 0.5M $H_2SO_4$ | — | 20 $mVs^{-1}$ | 10000 | — |
| 10 | TpOMe-DAQ | 1600 | 169 | 3M $H_2SO_4$ | 1531 | 0.35 A/g | 100000 | — |
| 11 | Ni3(HITP)2 | — | 111 | TEABF4/ACN | 630 | 0.05 A/g | 10000 | — |

TABLE 1-continued

Comparison of areal (mFcm$^{-2}$) and gravimetric (Fg$^{-1}$) capacitances with state-of-art promising electrode materials made up of different materials. Sr. No. 31 and 32 show data for the new monomer of formula M1 and polymer of formula P1

| Sr. No | Material | Specific Capacitance (mFcm$^{-2}$) | Gravimetric capacitance (Fg$^{-1}$) | Electrolyte used | Surface Area (m$^2$g$^{-1}$) | Scan Rate/ Current Density | Cycle | Ratio |
|---|---|---|---|---|---|---|---|---|
| 12 | [TEMPO] 100% NiP-COF | — | 167 | 0.1M (C$_4$H$_9$)$_4$NClO$_4$ | 5.2 | 0.1 A/g | — | [TEMPO] 100% NiP-COF:CB:PTFE (20:70:10) |
| 13 | graphene-based electrode | — | 154.1 | EMIM BF$_4$ ionic liquid electrolyte | — | 1 A/g | — | graphene, mixed with 5 wt % Super-P and 10 wt % PTFE |
| 14 | TCNQ-CTF-800 | — | 383 | 1M KOH | 3663 | 0.2 A/g | 5000 | TCNQ-CTFs:acetylene black:PTFE (80:10:10) |
| 15 | Aza-CMP@350 | — | 397 | 1M H$_2$SO$_4$ | 546 | 5 A/g | 10000 | Aza-CMP:acetylene black:PTFE (80:10:10) |
| 16 | Fe3O4/COF-5d | — | 112 | 0.5M H$_2$SO$_4$ | 872 | 0.5 A/g | 2000 | Fe3O4/COF-5d:CB:PTFE (80:10:10) |
| 17 | CAP-2 | — | 233 | 2M KCl | 594 | 1.0 A/g | 10000 | CAP-2:CB:PVDF (80:15:05) |
| 18 | TPDA-1 | — | 469.4 | 1M H$_2$SO$_4$ | 545 | 1 mVs$^{-1}$ | 1000 | — |
| 19 | TPC-1 | — | 424 | 6M KOH | 364 | 0.1 A/g | — | TPC-1:CB:PTFE (80:10:10) |
| 20 | TNN-550 | — | 298 | 1M H$_2$SO$_4$ | 1724 | 0.2 A/g | 5000 | TNN-550:CB:PTFE (85:10:05) |
| 21 | PAQs | — | 576 | 0.5M H$_2$SO$_4$ | 600 | 1 A/g | 6000 | PAQ:acetylene carbon:PTFE (80:15:05) |
| 22 | TpDAB | — | 335 | 1M Na$_2$SO$_4$ | 319 | 2 mVs$^{-1}$ | 1000 | PTFE (10 wt %) |
| 23 | PYBDA | — | 456 | 2M H$_2$SO$_4$ | 135 | 0.5 A/g | 15000 | PYBDA:acetylene black:PVDF (60:20:20) |
| 24 | PTCT-C | — | 558 | 6M KOH | 790 | 1.0 A/g | 1000 | PTCT-C:CB:PTFE (80:10:10) |
| 25 | TpPa-(OH)2 | — | 416 | 1M phosphate buffer | 369 | 0.5 A/g | 10000 (66% remain) | TpPa(OH)2:acetylene black:PVDF (75:10:15) |
| 26 | HTCP-700 | — | 445 | 1M H$_2$SO$_4$ | 2226 | 1 A/g | 10000 | HTCP-700:acetylene black:PVDF (80:10:10) |
| 27 | TCOP | — | 278 | 6M KOH | 2003 | 1 A/g | 3000 | TCOP:CB:PTFE (80:10:10) |
| 29 | IMPC | — | 258 | 1M H$_2$SO$_4$ | 1327 | 0.5 A/g | 5000 | IMPC:Conducting Carbon:Binder (80:15:05) |
| 30 | BIBDZ | — | 88.4 | 1M H$_3$PO$_4$ | 177 | 0.5 A/g | 5000 | — |
| 31 | P1 | 113 | 805 | 1M H$_2$SO$_4$ | — | 0.5 A/g | — | AM:Conducting Carbon:Binder (30:65:5) |
| 32 | M1 | 49 | 350 | 1M H$_2$SO$_4$ | — | 0.5 A/g | — | AM:Conducting Carbon:Binder (30:65:5) |

Figure 2:
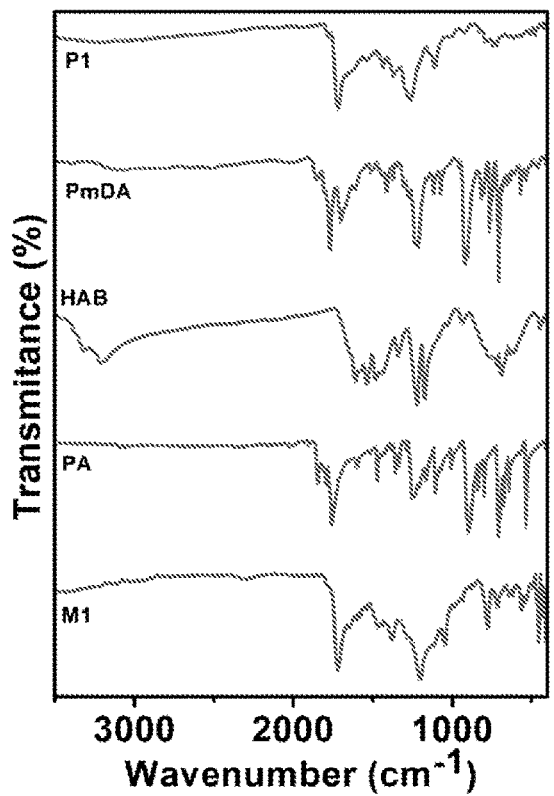
FIG. 2 shows the FTIR spectra of a monomer of formula M1 and polymer of formula P1.

The obtained samples are characterized by solid-state $^{13}$C NMR spectrum (Bruker-300 MHz NMR spectrometer instrument), Transmission electron microscopy (TEM, FEI Tecnai G2 F20 XTWIN), and Fourier transform infrared spectroscopy (Bruker Alpha FT-JR spectrometer) as shown in FIG. 1 and FIG. 2.

The cathode is prepared by casting a slurry of active material (AM), Activated Carbon (AC) and Nafion (binder) in Isopropyl Alcohol (IPA). The weight ratio of AM:AC: binder on the cathode is 3:6.5:0.5. The mass loading is per electrode area of ~140 μg cm$^{-2}$. The electrochemical experiments are carried out using Biologic (VMP 300) potentiostat. A standard three-electrode cell consisting of 3 mm diameter glassy carbon disk as the working electrode, Ag/AgCl (3.5 M KCl) as the reference electrode, and the Platinum counter electrode is used for electrochemical measurements. All solutions are prepared using Millipore water (18.2 MΩ·cm) and the cell temperature is maintained at 25° C. Electrochemical impedance spectroscopy (EIS) measurements are acquired in the frequency range of 100 kHz to 10 MHz with an AC amplitude of 10 mV (peak to peak) at a bias voltage of 0 V vs. OCV in $N_2$ saturated 1 M $H_2SO_4$ solutions.

Figure 3:
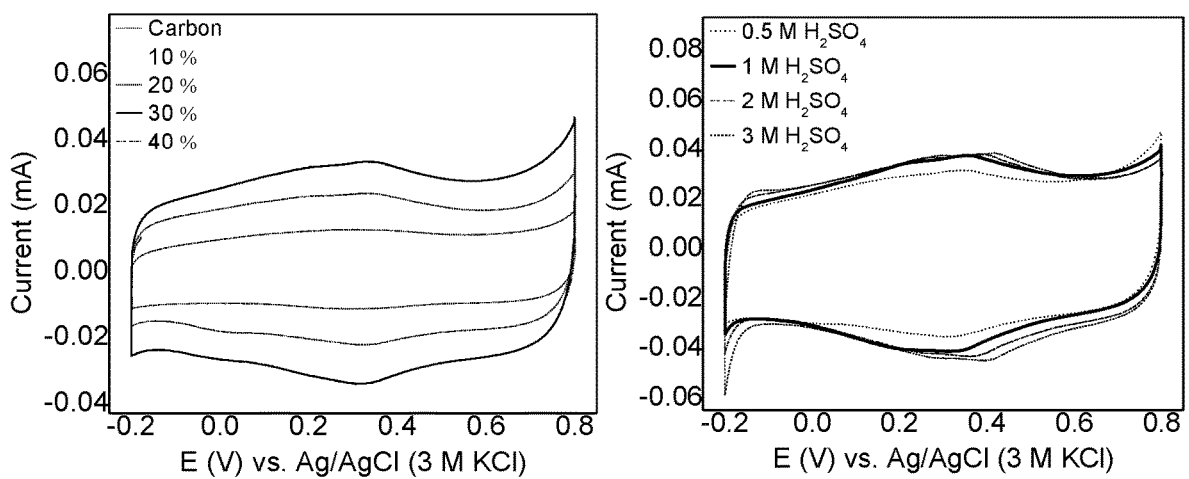
FIG. 3 shows cyclic voltammetry of polymer of formula P1 with optimization of Carbon percentage (left) and electrolyte concentration (right) in a three-electrode cell.
Figure 4:
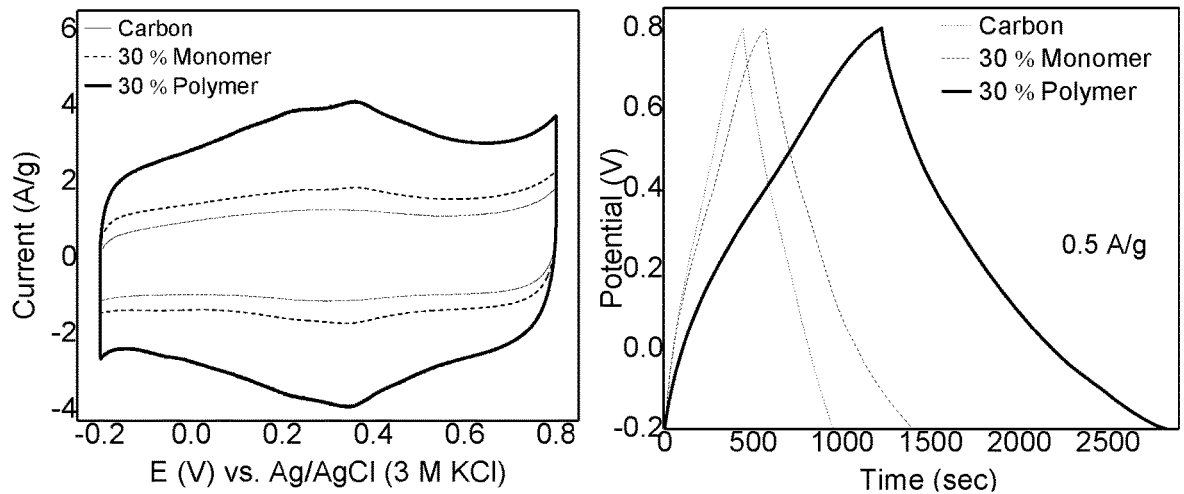
FIG. 4 depicts cyclic voltammetry (left) and Galvanostatic charge and discharge curves (right) at current densities of 0.5 A/g of Carbon, formula M1 and polymer of formula P1.

Different ratio of polymer with carbon has been taken for cyclic voltammetry (CV) measurements. Loading the material for the cathode electrode with 30% of the polymer gives enhanced capacitance. Similarly, electrolyte $H_2SO_4$ concentration has been changed from 0.5 M to 3.0M. There is no much enhancement in the performance of the device by changing electrolyte concentration as shown in FIG. 3. Both cyclic voltammetry (CV) and galvanostatic charge-discharge (GCDC) results show that the polymer of formula P1 exhibits enhanced capacitance than monomers M1 and Carbon, as shown in FIG. 4.

In the Galvanostatic charge and discharge (GCDC) experiment the constant current is applied to the sample and the potential is measured as a function of time. When the potential reaches the predetermined limit, charge polarities are reversed.

Figure 5:
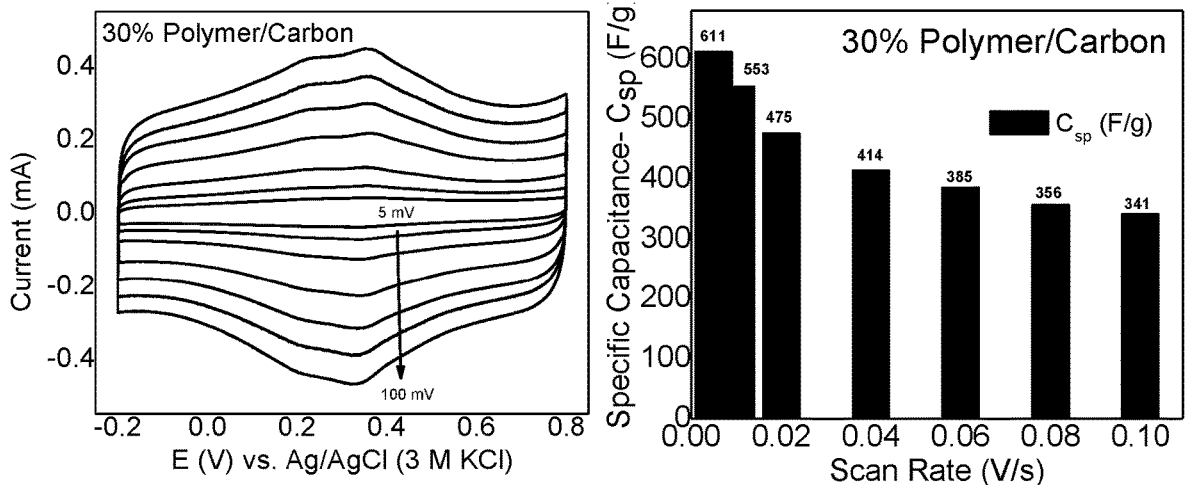
FIG. 5 shows cyclic voltammetry (left) with increasing scan rate from 5 mV to 100 mV and corresponding specific capacitance in F/g (right) of 30% P1/C.
Figure 6:
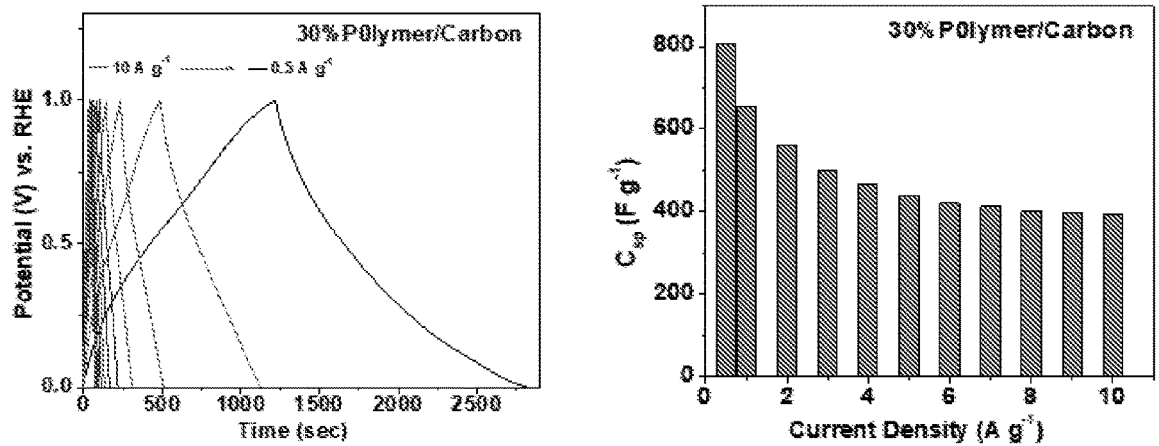
FIG. 6 shows Galvanostatic charge and discharge curves (left) with increasing current densities from 0.5 A/g to 10 A/g and corresponding specific capacitance in F/g (right) of 30% P1/C.
Figure 7:
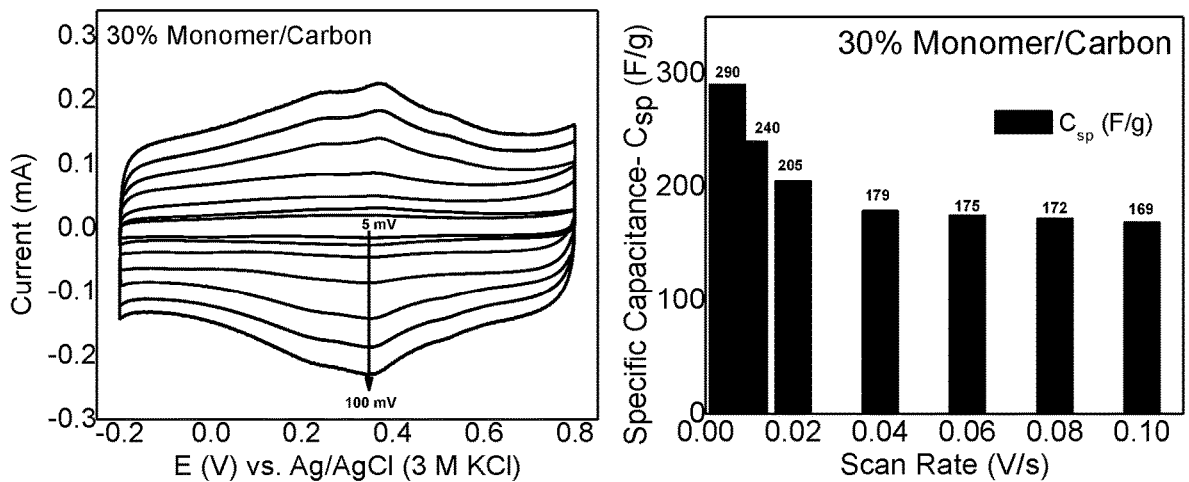
FIG. 7 shows cyclic voltammetry (left) with increasing scan rate from 5 mV to 100 mV and corresponding specific capacitance in F/g (right) of 30% M1/C.
Figure 8:
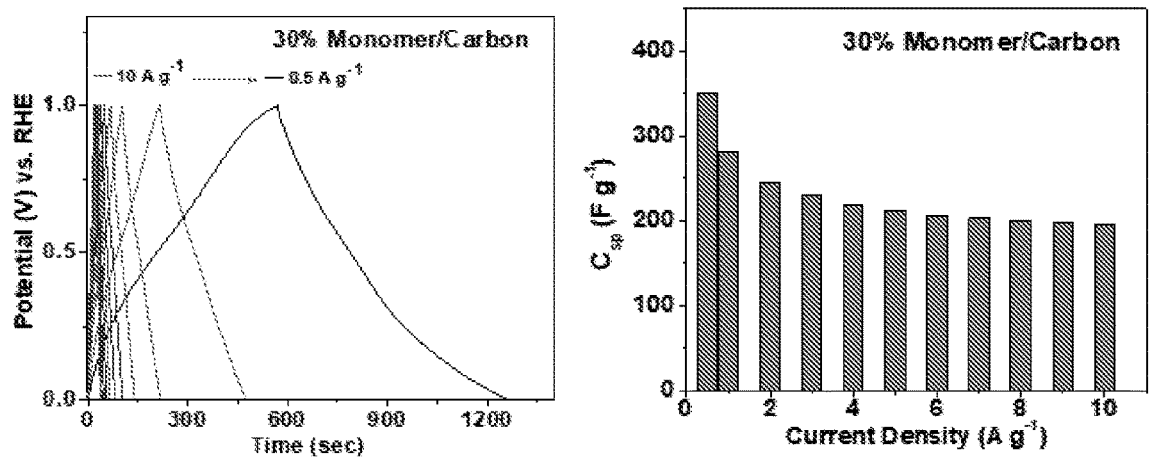
FIG. 8 shows Galvanostatic charge and discharge curves (left) with increasing current densities from 0.5 A/g to 10 A/g and corresponding specific capacitance in F/g (right) of 30% M1/C.
Figure 9:
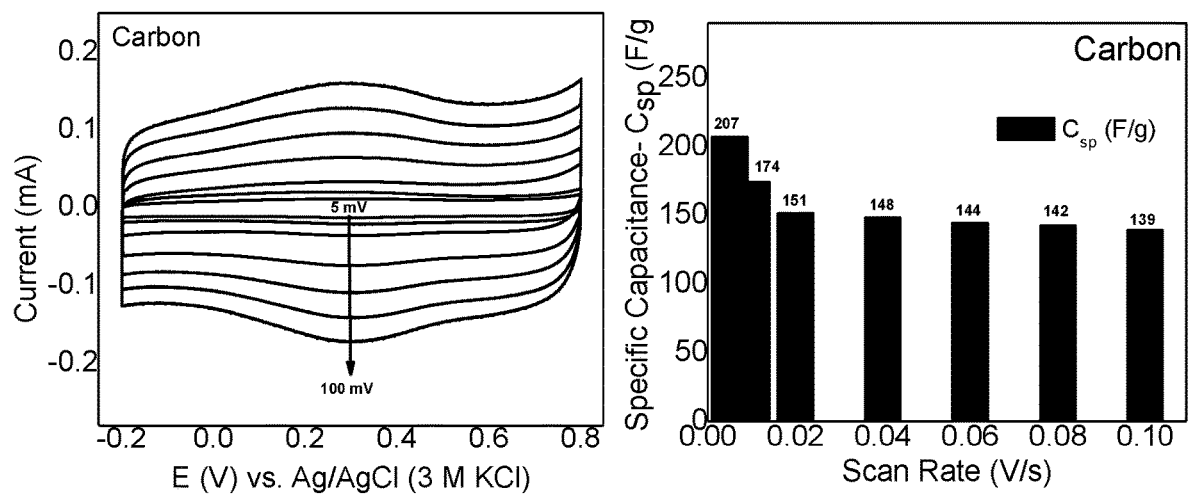
FIG. 9 shows cyclic voltammetry (left) with increasing scan rate from 5 mV to 100 mV and corresponding specific capacitance in F/g (right) of Carbon.
Figure 10:
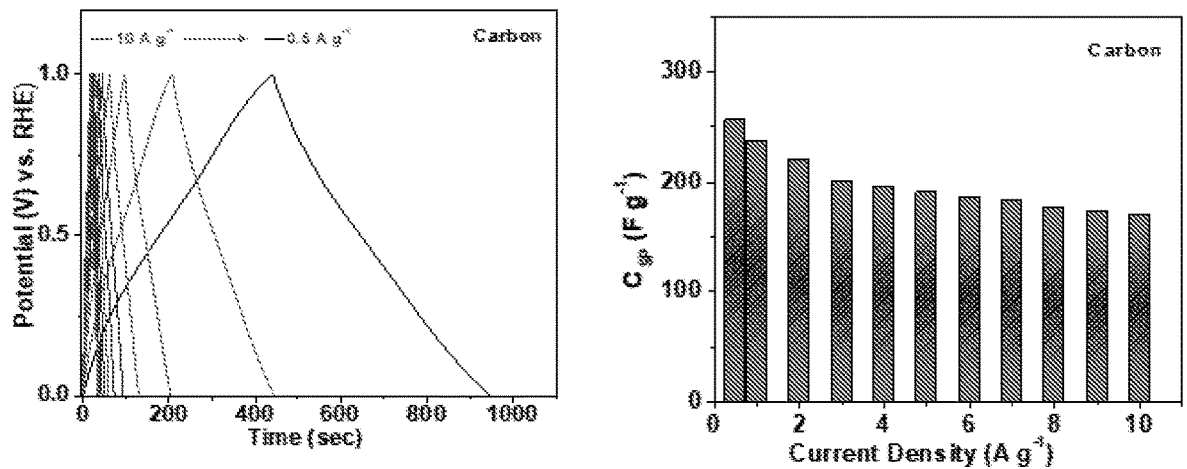
FIG. 10 depicts Galvanostatic charge and discharge curves (left) with increasing current densities from 0.5 A/g to 10 A/g and corresponding specific capacitance in F/g (right) of Carbon.
Figure 11:
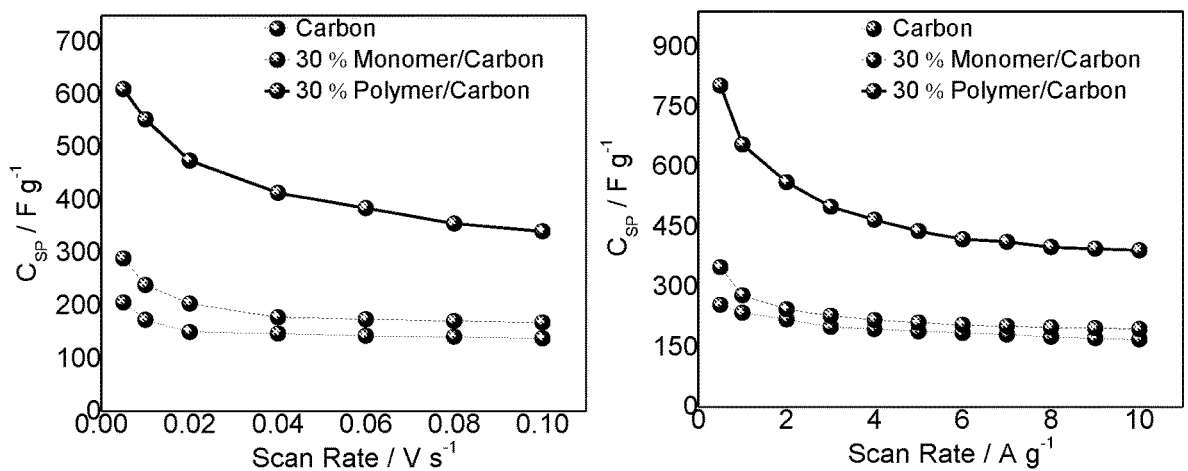
FIG. 11 depicts the Comparison of specific capacitance in F/g of 30% P1/C, 30% M1/C and Carbon, from CV (left) and from Galvanostatic charge and discharge (right).

Cyclic voltammetry (CV) experiments with increasing scan rate from 5 mV to 100 mV of the polymer of formula P1 show decrease in specific capacitance from 611 F/g to 341 F/g as shown in FIG. 5. For monomer of formula M1 and alone carbon the specific capacitance at higher scan rate is observed 169 F/g and 139 F/g, respectively as depicted by FIG. 7 and FIG. 9. Galvanostatic charge and discharge (GCDC) experiments of the polymer of formula P1 at current densities of 0.5 to 10 A/g are carried out. The specific capacitance gradually increases from 392 F/g to 805 F/g, while the current density decreases up to 0.5 A/g as shown in FIG. 6. Similarly, for the monomer of formula M1, the capacitance value is at 0.5 A/g and current density is at 350 F/g and alone carbon shows capacitance 258 F/g at the same current density as depicted in FIG. 8 and FIG. 10. Comparison of specific capacitance of polymer of formula P1, monomer of formula M1 and alone carbon is calculated from both CV and GCDC experiments with different scan rates and current densities as shown in FIG. 11.

EXAMPLES

The following examples are given by way of illustration, therefore, should not be construed to limit the scope of the invention.

Example 1: Synthesis of a Monomer of Formula M1

151 mg (1 eq.) of HAB and 800 mg (6 eq.) of phthalic anhydride were mixed into 50 mL of DMSO. The reaction mixture was refluxed (180° C.) under argon (1 atm) for 24 h. After completion of the reaction (precipitate obtained), the remaining DMSO was distilled out (180° C.) with a downward distillation method. The final product was centrifuged and washed with deionized water and acetone to get solid powder. The powder collected and then soxhlet extraction was performed with water, methanol, acetone for 36 hours and then dried under vacuum to give a dark green solid, 794 mg. Yield (Isolated): 93%.

Example 2: Synthesis of the Polymer of Formula P1

300 mg (1 eq.) of HAB and 1.17 g (3 eq.) of pyromellitic dianhydride were mixed into 70 mL of DMSO. The reaction mixture was refluxed (180° C.) under argon (1 atm) for 24 h. After completion of the reaction (precipitate obtained), the remaining DMSO was distilled out (180° C.) with a downward distillation method. The final product was centrifuged and washed with deionized water and acetone to get solid powder. The powder collected and then soxhlet extraction was performed with water, methanol, acetone for 36 hours and then dried under vacuum to give a dark black solid, 1.20 g. Yield (Isolated): 94%.

Example 3: Synthesis of the Monomer of Formula M2

1 equivalent of HAB and 6 equivalent of 1H,3H-benzo[de]isochromene-1,3-dione (NMA) was mixed into 50 mL of DMSO. The reaction mixture was refluxed (180° C.) under argon (1 atm) for 24 h. After completion of the reaction (precipitate obtained), the remaining DMSO was distilled out (180° C.) with a downward distillation method. The final product was centrifuged and washed with deionized water and acetone to get solid powder. The powder was collected and then soxhlet extraction was performed with water, methanol, acetone for 36 hours and then dried under vacuum to give a monomer M2.

Example 4: Synthesis of the Polymer of Formula P2

1 equivalent of HAB and 3 equivalent of Isochromeno[6,5,4-def]isochromene-1,3,6,8-tetrone (NDA) was mixed into 70 mL of DMSO. The reaction mixture was refluxed (180° C.) under argon (1 atm) for 24 h. After completion of the reaction (precipitate obtained), the remaining DMSO was distilled out (180° C.) with a downward distillation method. The final product was centrifuged and washed with deionized water and acetone to get solid powder. The powder was collected and then soxhlet extraction was performed with water, methanol, acetone for 36 hours and then dried under vacuum to give a polymer P2.

Advantages of the Invention

The present invention provides the first Electric double-layer capacitors (EDLC) based on HAB derivative and showing the highest specific capacitance.

The present invention thus establishes a new family of active materials for EDLCs.

The process has synthetic versatility to prepare new derivatives which can help to achieve better performance devices for energy storage.

The excellent cyclic stability, reduced self-discharge rate, high energy, and power densities, and extremely high CSP support the 2D-polymer as a promising supercapacitor material for futuristic portable electronic devices.

The present design strategy paves the way for new 2D-polymer design and widens the scope of organic-based materials for supercapacitor applications.

The invention claimed is:

1. A two-dimensional organic monomer of formula (M);

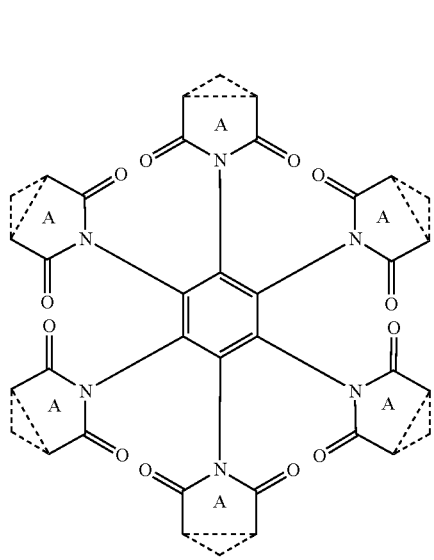

(M)

wherein:
each ring A is a 5-membered ring or a 6-membered ring;
when a ring A is a 5 membered ring, the ring A is fused with a benzene ring at a dotted bond of the ring A; and
when a ring A is a 6 membered ring, the ring A is fused with two fused benzene rings at two dotted bonds of the ring A.

2. The two-dimensional organic monomer of claim 1, selected from the group consisting of a monomer of formula (M1) and a monomer of formula (M2):

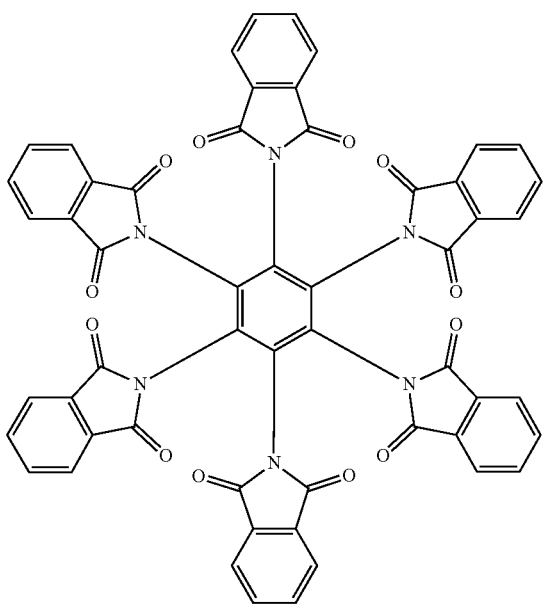

(M1)

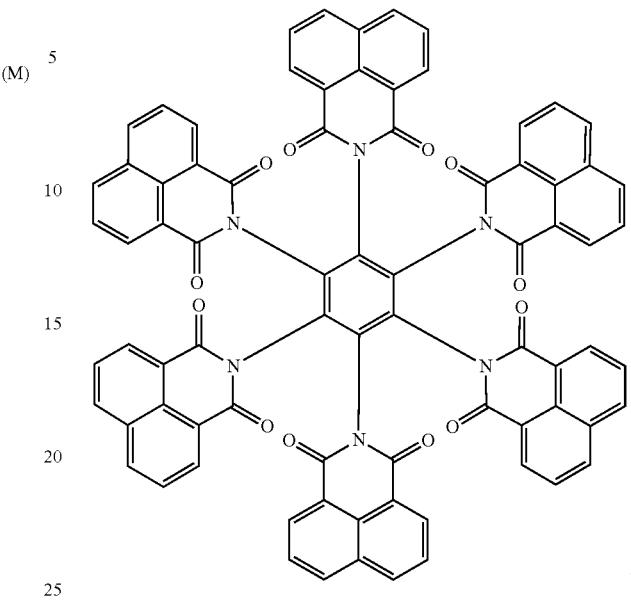

(M2)

3. A process for preparing the two-dimensional monomer according to claim 1, the process comprising:
(i) charging hexaaminobenzene (HAB) and an anhydride compound in a DMSO solvent to obtain a reaction mixture, the anhydride compound having formula (1):

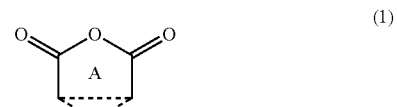

(1)

where:
ring A is a 5-membered ring or a 6-membered ring;
when ring A is a 5-membered ring, the ring A is fused with a benzene ring at a dotted bond of the ring A; and
when a ring A is a 6-membered ring, the ring A is fused with two fused benzene rings at two dotted bonds of the ring A;
(ii) refluxing the reaction mixture under argon atmosphere for 20 hours to 24 hours;
(iii) distilling the reaction mixture at 170° C. to 190° C. and 0 atm to 5 atm pressure to obtain a solid;
(iv) centrifuging the solid obtained from (iii) and washing the solid with water and acetone solvent;
(v) performing a soxhlet extraction on the solid obtained from (iv) with water, methanol, and acetone for 35 hours to 40 hours; and
(vi) drying the solid obtained from (v) under vacuum at 80° C. to obtain the two-dimensional organic monomer having formula (M).

4. The process of claim 3, wherein the anhydride compound of Formula (1) is selected from phthalic anhydride and 1H,3H-benzo[de]isochromene-1,3-dione (NMA).

5. A polymer of the two-dimensional monomer according to claim 1, the polymer being selected from a polymer having a repeat unit according to formula (P1):

(P1)

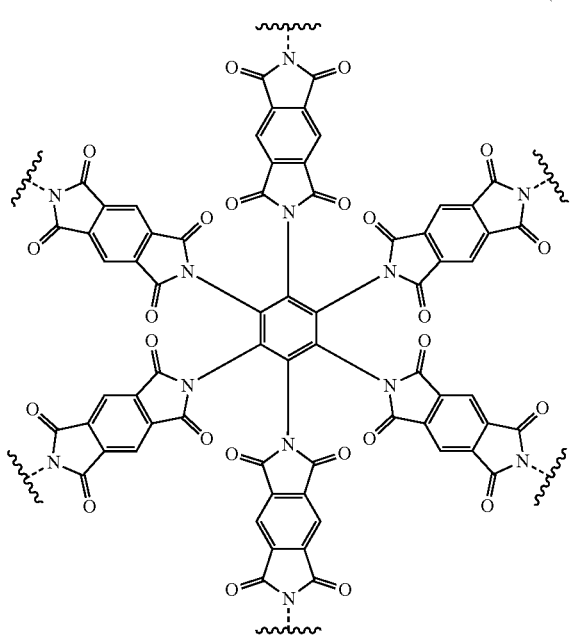

and a polymer having a repeat unit according to formula (P2):

(P2)

6. A process for preparing a polymer of the two-dimensional organic monomer according to claim 1, the process comprising:
charging hexaaminobenzene (HAB) and a dianhydride compound in a DMSO solvent to obtain a reaction mixture;
(ii) refluxing the reaction mixture under argon atmosphere for 20 hours to 24 hours;
(iii) distilling the reaction mixture at 170° C. to 190° C. and 0 atm to 5 atm pressure to obtain a solid;
(iv) centrifuging the solid obtained from (iii) and washing the centrifuged solid with water and acetone solvent;
(v) performing a soxhlet extraction on the solid obtained from (iv) with water, methanol, and acetone for 35 hours to 40 hours; and
(vi) drying the solid obtained from (v) under vacuum at 80° C. to obtain the polymer.

7. The process of claim 6, wherein the dianhydride compound is selected from pyromellitic dianhydride and isochromeno[6,5,4-def]isochromene-1,3,6,8-tetrone (NDI).

8. A composition for supercapacitor applications, the composition comprising a polymer according to claim 5, a binder, and carbon.

9. The composition of claim 8, comprising, based on the total weight of the composition:
30% by weight polymer;
5% by weight binder; and
65% by weight carbon.

10. The composition of claim 9, wherein the composition has a specific capacitance of 805 F/g at 0.5 A/g.

* * * * *